United States Patent [19]

Mondal et al.

[11] Patent Number: 5,693,526
[45] Date of Patent: Dec. 2, 1997

[54] STRAINS OF YEAST OF SACCHAROMYCES CEREVISIAE AND A PROCESS FOR THE PREPARATION OF SUCH STRAINS OF YEAST

[75] Inventors: Alok Kumar Mondal; Gandham Satyanarayana Prasad; Tapan Chakrabarti, all of Chandigarh, India

[73] Assignee: Council of Scientific & Industrial Research, New Delhi, India

[21] Appl. No.: 625,000

[22] Filed: Mar. 29, 1996

[51] Int. Cl.⁶ .................................................. C12N 1/16
[52] U.S. Cl. .................. 435/255.2; 435/171; 435/172.2; 435/255.1; 435/255.21; 426/7; 426/11; 426/60; 426/62
[58] Field of Search .................... 435/255.2, 255.21, 435/171, 255.1, 172.2, 942; 426/7, 60, 62, 11

[56] References Cited

U.S. PATENT DOCUMENTS 5,353,606  10/1994  Takano et al. ...................... 435/255.2

FOREIGN PATENT DOCUMENTS

2616445 A  12/1988  France .

OTHER PUBLICATIONS

Yezinhet et al., Introduction of Flocculation into an Industrial Yeast Strain by Transfer of a Single Chromosome, J.Inst. Brew 98315319, 1992.

Romano et al, Improvement of a Wine *Saccharomyces cerevisiae* Strain by a Breeding Program, Appl. Environ. Microb 50(4):1064–1067, 1985.

*Primary Examiner*—Blaine Lankford
*Attorney, Agent, or Firm*—Darby & Darby

[57] ABSTRACT

The present invention relates to a novel strain of the yeast *Saccharomyces cerevisiae* having accession number MTCC Y0022B211 (=NCYC 2647), which is useful for the preparation of ethanol by the fermentation of sugars. The invention also encompasses a process for the preparation of this strain of yeast, which process comprises: (a) growing a diploid strain of *S. cerevisiae* designated MTCC Y0001 (=NCYC 2646) in a known medium, sporulating the strain, treating the sporulated cells with a lytic enzyme to liberate the spores, collecting the liberated spores; (b) growing a haploid strain of *S. cerevisiae* designated MTCC Y0002 (=ATTC 90506); (c) mixing the spores obtained in step (a) with the cells obtained in step (b), incubating the resultant spore-cell mixture at a temperature in the range of 15° C. to 37° C. for a period of 1 to 10 days; (d) spreading the incubated spore-cell mixture on a non-medium, and incubating the mixture at a temperature in the range of 15° to 37° C. for a period of 1 to 10 days; and (e) collecting the cells produced in step (d); and spreading on a selective medium so as to eliminate the spores and cells of steps (a) and (b) and allowing only hybrid cells/cytoductants to grow.

6 Claims, No Drawings

STRAINS OF YEAST OF SACCHAROMYCES CEREVISIAE AND A PROCESS FOR THE PREPARATION OF SUCH STRAINS OF YEAST

FIELD OF THE INVENTION

The invention relates to a new strain of the yeast *Saccharomyces cerevisiae* having accession number MTCC Y0022B211 (=NCYC 2647) and a process for the preparation of new strains of the yeast *Saccharomyces cerevisiae* useful for the production of ethanol by the fermentation of sugars. The ethanol so prepared is useful both for potable and industrial purposes.

BACKGROUND OF THE INVENTION

It is well known that ethanol or ethyl alcohol ($C_2H_5OH$) can be produced by both fermentation and synthetic methods. Fermentation techniques for ethanol production developed during the early part of this century were supplemented by synthetic processes based on crude petroleum, as oil was much cheaper and abundantly available. However, of late, it has been realized that the petroleum oil reserve is limited; consequently, the fermentative production of ethanol has again picked up, using various kinds of renewable fermentable substrates, such as: (i) sugar (from sugar-cane, sugar beet, fruit) which may be converted to ethanol directly; (ii) starch (from grain, root crops) which is first hydrolysed to fermentable sugars by enzymes; and (iii) cellulose (from wood, agricultural wastes, etc.) which is converted to sugars. (*Biotechnology: Economic and Social Aspects—Issues for Developing Countries*, Eds. E. J. Da Silva, C. Ratiedge and A Sesson; Cambridge University Press, p.24, 1992).

Ethanol production by fermentation is based mainly on yeasts, and for large scale fuel production, these are generally of the genus Saccharomyces.

Distillers all over the world would like to have a fermentation process that yields a high percentage of alcohol in the broth without sacrificing fermentation efficiency. The primary benefits of such an operation are:

a) The potential to increase the productivity of the fermenter (wherein productivity is defined as the mount of alcohol produced per unit fermenter volume per hour).

b) A saving in energy/steam requirement during distillation, energy being the major variable cost in distillery operation.

c) A reduction in the volume of effluent.

d) Using flocculent yeast strains, fermentation may be achieved by recycling of cells, whether in a continuous mode or by a conventional batch mode. Because of their flocculent nature, the cells are easily separated from the fermented broth; in a recycling mode or in a continuous mode, less sugar is expected to be required for accumulation of biomass.

In conventional methods of ethanol production, the initial concentration of sugar in the broth is maintained at a concentration between 14 to 16 percent. Sugar concentrations higher than this are detrimental to growth of yeast strains used in conventional processes, and fermentation is thus affected. After completion of fermentation, 6.5 to 8 percent alcohol is obtained in the wash. Alcohol is then recovered by distillation using steam.

In order to achieve higher ethanol levels in the wash, the initial sugar concentration in the broth should also be higher, thereby increasing the osmolarity of the medium which is detrimental to the growth and fermentation of the conventional yeast strains. Conventional strains are also sensitive to high levels of ethanol in the broth, and, furthermore, they do not have flocculent characteristics.

The main drawback of conventional yeast strains is their failure to grow and remain active at high sugar concentrations during the fermentation process that produces ethanol. At the same time, unless a high sugar concentration is used in the fermentation process, it is not possible to obtain an increased level of ethanol. Concurrent with this problem, conventional yeasts will not be effective in fermentation if the ethanol concentration is increased in the broth. The cumulative effect of these problems in the conventional process of production of ethanol is a low level of ethanol produced in the wash; consequently, consumption of steam per liter of ethanol distilled is high. Therefore, the processes are not efficient and also not economical. Moreover, separation of conventional yeast strains from fermented broth is not easy and may not be very efficient in a cell-recycling or continuous mode of operation.

PRIOR ART OF THE INVENTION

A strain of *Saccharomyces cerevisiae* designed MTCC Y0001 was developed and deposited at the Microbial Type Culture Collection and Gene Bank located at the Institute of Microbial Technology, Chandigarh, India, a constituent laboratory of the Council of Scientific and Industrial Research, India. This strain has also been deposited on Mar. 11, 1996, at the National Collection of Yeast Culture (NCYC), Institute of Food Research, Norwich Laboratory, Norwich Research Park, Colney, Norwich, NR4 7UA, United Kingdom, an International Depository Authority (DA) under Budapest Treaty and has been assigned the designation NCYC No. 2646. This strain is osmotolerant and ethanol tolerant, and produces high percentage of alcohol. This strain is disclosed in copending Indian patent application number 748/DEL 93.

Another *Saccharomyces cerevisiae* strain having accession number MTCC Y0002 (=ATCC 90506) was used for producing the novel and improved varieties of strains of *Saccharomyces cerevisiae* designated as MTCCY0001. Strain MTCCY0002 has auxotrophic markers, is resistant to an antibiotic, is flocculating, is defective in karyogamy, and is haploid and of the alpha mating type.

Realizing the need to have strains possessing various desirable properties and useful for high density fermentation, we continued our research with the objective of developing flocculent strains of yeast which, in addition to tolerating high initial sugar concentration, i.e., having osmotolerant characteristic, could survive in the higher concentration of ethanol it produces in the broth. In other words, the strain to be used should be tolerant to high concentrations of ethanol produced during the fermentation. For use in different modes of operations, the flocculent characteristic in the strain is also desirable. That is, in order to achieve fermentation using cell-recycling, repeated batch fermentation, or continuous mode, it is desirable that the strain is of the flocculent type (in addition to retaining other desirable properties). One advantage of this unique type of strain is that less sugar is utilized to accumulate biomass, and the sugar thus saved may be converted to ethanol. Moreover, if such a strain is flocculating, there is less wash-out of the cell during operation of the process. Such a strain should also give higher productivity of ethanol. In addition, a high concentration of ethanol in the wash results in a reduction in steam requirements for distillation. Since the strains used in conventional distilleries produce 6.5 to 8 percent alcohol in the wash and have a fermentation efficiency of 82.90–86.90 percent (Arbatti, S. V. and Kale, V. M., *Proceedings of International Seminar on Modernization of Distilleries and Breweries*, organized by All India Distillers Association, July 1969), we concentrated our research on the development of an improved strain of *Saccharomyces cerevisiae* having flocculent characteristics, capable of producing 7 to 12% or more alcohol in the wash, with a fermentation efficiency which is as good as, if not better than, processes employing conventional yeast strains.

SUMMARY AND OBJECTS OF THE INVENTION

The main object of the present invention is, therefore, to provide a novel strain of the yeast *Saccharomyces cerevisiae*, designated MTCC Y0022B211 (=NCYC 2647), which is produced by genetic hybridization and cytoduction and is useful in fermentation processes for the production of ethanol.

A further object of the present invention relates to a process for the preparation of a novel strain of the yeast *Saccharomyces cerevisiae*, designated MTCC Y0022B211 (=NCYC 2647), which is produced by genetic hybridization and cytoduction and is useful in fermentation processes for the production of ethanol.

The new strain has been deposited in the National Facility of Microbial Type Culture Collection and Gene Bank (MTCC) located at the Institute of Microbial Technology, Chandigarh, India, a constituent laboratory of Council of Scientific and Industrial Research, India. This strain has also been deposited at National Collection of Yeast Cultures (NCYC), Institute of Food Research, Norwich Laboratory, Norwich Research Park, Colney, Norwich, NR4 7UA, U.K., an IDA under Budapest Treaty on Mar. 11, 1996, and has been assigned the number NCYC 2647.

DETAILED DESCRIPTION OF THE INVENTION

In general, desirable genetic properties of two yeast strains, MTCC Y0001 (=NCYC 2646) and MTCC Y0002 (=ATCC 90506), or more, may be combined to create novel strains. This may be achieved by any means known in the art, including, without limitation, mating, crossing, genetic hybridization, cytoduction, protoplast fusion, as well as by genetic engineering and expression of cloned gene(s). To accomplish these manipulations in the laboratory, the strain needs to contain appropriate genetic markers, and an innovative method has to be developed for the production of the improved and novel strains.

The starting yeast strains of the present process, i.e., MTCC Y0001 and MTCC Y0002, as well as the newly produced strains, have been deposited in the National Facility on Microbial Type Culture Collection and Gene Bank (MTCC) located at the Institute of Microbial Technology, Chandigarh, India, a constituent laboratory of Council of Scientific and Industrial Research, India. The yeast strain MTCC Y0001 was also deposited on Mar. 11, 1996, at the National Collection of Yeast Culture, U.K., and has been assigned accession number NCYC 2646.

Accordingly, the present invention provides a process for the preparation of a novel strain of the yeast *Saccharomyces cerevisiae* having the accession number MTCC Y0022B211 (=NCYC 2647) deposited at the Microbial Type Culture Collection and Gene Bank located at the Institute of Microbial Technology, Chandigarh, India, a constituent laboratory of Council of Scientific and Industrial Research, India, and also at the National Collection of Yeast Culture, U.K., an International Depository authority under Budapest Treaty, which process comprises:

a) growing a diploid strain of the yeast *Saccharomyces cerevisiae* designated MTCC Y0001 (=NCYC 2646), sporulating the strain, treating the sporulated cells with a known lyric enzyme to liberate the individual spores, and collecting the liberated spores;

b) growing a haploid strain of yeast *Saccharomyces cerevisiae* designated as MTCC Y0002 (=ATTC 90506), and collecting the cells;

c) mixing the spores obtained in step (a) with the cells obtained in step (b) and incubating the resultant spore-cell mixture at a temperature in the range of about 15° C. to about 37° C. for a period from about 1 to about 10 days;

d) spreading the incubated spore-cell mixture obtained in step (c) on a non-selective growth medium and incubating the mixture at a temperature in the range of about 15° C. to about 37° C. for a period of about 1 to about 10 days;

e) collecting the cells produced in step (d), and spreading the cells on a selective medium so as to eliminate the spores and cells of steps (a) and (b) and allow only hybrid cells/cytoductants to grow; and f) purifying the hybrid cells/cytoductants.

The medium used for sporulating the diploid strain MTCC Y0001 may be any appropriate medium known in the art, such as, for example, a medium comprising agar, yeast extract, dextrose, potassium acetate, and distilled water. The lytic enzymes that may be used to liberate the spores include without limitation lyticase, glusulase, and zymolyase.

The haploid strain MTCC Y0002 used in step (b) may be selected from a haploid strain as such or a haploid strain obtained from diploid strains. By way of example, other properly marked strains may also be used.

The haploid strain in step (b) is grown in any appropriate medium known in the art, such as, for example, YEPD (Yeast extract peptone, dextrose), at a temperature in the range of about 15° C. to about 35° C. for a period of about 1 to about 10 days. The ratio of the strains MTCC Y0001 and MTCC Y0002 used in step (c) may range from about 20:1 to about 1:20.

The incubation in steps (c) and (d) may be effected at a temperature in the range of about 15° to about 37° C. for a period in the range of about 1 to about 10 days. The non-selective medium used in step (d) may be selected from SD Medium (yeast nitrogen base, dextrose, agar and distilled water), YPD (yeast extract, peptone, dextrose, agar and distilled water), or YPG (yeast extract, peptone, glycerol, agar and distilled water).

The selective medium used in step (e) may be any appropriate medium known in the art, such as, for example, SDG (yeast nitrogen base, dextrose, glycerol, agar and distilled ater) fortified with a broad-range antibiotic, including without limitation geniticin, oligomycin, chloramphenicol and combinations thereof.

The different strains are isolated by conventional methods well-known in the art, such as streaking or dilution plating.

The details of the steps of the process of the present invention are as follows.

The parental strain designated MTCC Y0001 is homothallic and produces spores of both a mating type and alpha mating type. This strain is sporulated in any appropriate medium, the spores are released by dissolving the ascus wall by enzymatic treatment, and the spores are then collected. These spores and the cells (spores) of the other strain (designated MTCC Y0002) are mixed in different ratios. After incubation at a temperature in the range of about 10° C. to about 37° C., the mixture is spread over non-selective medium to allow for growth of cells. The population of cells is then spread on selective medium. The selective medium is designed so that the original two strains (Y0001 and Y0002) do not survive. Only hybrids created by transfer of desirable genetic material from Y0001 to Y0002 (and vice versa) are able to grow, and there were many such hybrids or cytoductants. The hybrids or cytoductants produced are then initially screened for flocculation. In general, some strains show flocculation, while others do not. Among the flocculent hybrids (or cytoductants), three types are apparent. These are (i) good (sedimentation time of 10–20 seconds); (ii) moderate (sedimentation time of 20–35 seconds); and (iii) slow (sedimentation time of 35–60 seconds).

The strain produced by this procedure is novel and its characteristics are given in Table 1.

TABLE 1

|  | Hybrid/cytoductant |
| --- | --- |
| Antibiotic resistance | + |
| Auxotrophy | − |
| Flocculation | + |
| Growth on: |  |
| a) 40% molasses | + |
| b) 50% molasses | + |
| ethanol production | 7–12% |

Electrophoretic karyotyping of the hybrid reveals a different pattern from that obtained with either MTCC Y0001 or MTCC Y0002. This strain has been assigned the following accession number: MTCC Y0022B211 (=NCYC 2647).

The new strain prepared by the process of the present invention has the following characteristics:

i) It grows at temperatures ranging between about 15° C. to about 37° C. in Yeast Extract Peptone Dextrose (YEPD) medium containing 2% glucose.

ii) It grows on agar plates containing molasses at concentrations of up to 50%, and does not need any additional nutritional supplementation when grown in this medium.

iii) It produces 7% to 12% (v/v) ethanol at 30° C., with a fermentation efficiency of 90% or more.

iv) It grows in Yeast Extract Peptone Dextrose (YEPD) medium in presence of 12% ethanol. The strain is, therefore, osmotolerant and ethanol tolerant and produces a high level of alcohol.

v) The cells show flocculation in liquid medium, such as, Yeast Extract Peptone Dextrose (YEPD), Yeast Extract Peptone Sucrose (YEPS), or medium containing molasses.

vi) It is resistant to an antibiotic.

vii) It sporulates and produces ascospores.

viii) Its properties as described above are quite stable.

ix) It retains its fermentation ability for use in recycling.

x) Under appropriate conditions of flocculation, it settles or sediments within 10–55 seconds.

The biochemical properties of the new strain are that it utilizes glucose, sucrose, maltose, saccharose and raffinose as carbon sources, but does not grow on salicin, lactose, inositol, citrate, 2-Keto-D-gluconate, arabinose, xylose, adanitol, xylitol, sorbitol, methyl-D-glycoside, n-acetyl-glucosamine, cellobiose, trehalose, or melizitose. Growth is poor when sodium nitrate, potassium nitrate or lysine are used as a sole source of nitrogen.

Molasses is a by-product of the sugar manufacturing process. What remains after sugar is extracted from sugar cane juice is known as molasses. This by-product still contains some sugar, the concentration of which depends on the efficiency of sugar extraction. A good quality (Grade A) molasses contains a minimum of 55% (w/v) sugar. A Grade C molasses, on the other hand, has about 40% (w/v) sugar. In order to achieve a desired sugar concentration in a fermenter, molasses is accordingly diluted with water.

Since ethanolic fermentation is a process by which certain microorganisms convert sugars such as sucrose, glucose and fructose to ethyl alcohol, the sugars that can be used in the process of the present invention include, without limitation, glucose, sucrose, fructose or other reducing sugars, either added as solids or as present in molasses, or a combination of these; or may comprise the sugars obtained from starch and other lignocellulosic material.

The description given above indicates that the process of the present invention results in a new yeast strain, which has improved characteristics and which can be utilized for the production of high percentage of ethanol. The process results in yeast strains having synergistic characteristics.

The process of the present invention is illustrated in the examples given below, which should not, however, be construed to limit the scope of the present invention.

EXAMPLE 1

A strain of *Saccharomyces cerevisiae* MTCC Y0001 (=NCYC 2646) was grown in YEPD (yeast extract, peptone, dextrose, distilled water) medium and then spread on pre-sporulation medium (yeast extract, peptone, dextrose, agar, distilled water) and incubated for 48 hours at 25° C. Cells were harvested and spread over sporulation medium and incubated at 25° C., and samples were observed under the microscope to monitor the progress of sporulation (which usually takes 3 to 7 days). The asci (structures containing spores) were harvested, treated with zymolyase to liberate the spores, and a random spore suspension was made. The other strain, MTCC Y0002 (=ATCC 90506), was grown in YEPD. Suspensions of the MTCC Y0001 spores and the MTCC Y0002 cells were mixed in 1:10 ratio, spread on YEPD medium, and incubated at 25° C. for 16 hours. The mixture was then spread on Complete Yeast Nitrogen Base Glucose medium and incubated at 25° C. Cells from above plates were harvested and spread on Yeast Nitrogen Base Glycerol (YNBG) medium containing oligomycin. Cells growing on these plates were considered hybrids or cytoductants. Following growth, they were screened for transfer of desired genetic properties.

Hybrids or cytoductants as generated by methods described above were purified to single colonies on YNBG selective plates.

Flocculation: Cells were inoculated into 2 ml YEPD medium in 24-well microtitre plates. The plates were incubated at 30° C. with shaking (150 rpm) for 24 to 48 hours. Flocculation was observed as the accumulation of the majority of the cells in a given well as small granules at the bottom of the well.

Flocculation could also be visualized in flasks containing liquid medium, such as, YEPD, YEPS, buffered YNB Glucose, molasses, etc. Genetically improved hybrids (cytoductants) were grown in YEPD for 16 hours at 30° C. Cells from this culture were inoculated separately into 100 ml of clarified molasses in conical flasks, incubated at 30° C.

with shaking (150 rpm). Growth and fermentation, as determined by the loss of weight of the flasks, was monitored at regular intervals up to 24 hours. The contents of each flask were quickly poured into graduated measuring cylinders. The time taken for the flocculated cells to sediment to the bottom was recorded with the help of a stop watch. For example, MTCC Y0022B211 had a sedimentation time of 34 to 35 seconds.

Ethanol production: The new strain was inoculated into YEPD and incubated at 25° C. with shaking for 24 hours. Samples were added to fresh YEPD medium containing 17% (v/v) sugar. The flasks were incubated at 30° C. with shaking. Samples were withdrawn at regular intervals, and incubation continued up to 48 hours. The sugar content and alcohol concentration produced in each sample were determined by the standard anthrone method and potassium dichromate methods, respectively. This strain produces between 7% to about 12% alcohol.

EXAMPLE 2

*Saccharomyces cerevisiae* strain MTCC Y0001 (=NCYC 2646) was grown in liquid YEPD medium for 16 hours at 30° C. The cells were then transferred to a flask containing liquid presporulation medium and incubated at 30° C. for 16 hours. The cells were then transferred to liquid sporulation medium in a flask and were incubated at 30° C. for 2 to 5 days. When majority of the cells were found to have formed asci, each containing 2 to 4 spores, the cells (asci) were centrifuged, suspended in a buffer and treated with lyticase to release the spores. The released spores were harvested by centrifugation and re-suspended. Strain MTCC Y0002 (=ATCC 90506) was grown in YEPD.

Suspensions of the two strains were mixed in a 10:1 ratio, spread on YEPD plates, and incubated at 30° C. for 16 hours. The mixture was then spread on Complete Yeast Nitrogen Base Glucose (YNBG) medium and incubated at 30° C. Cells from above plates were harvested and spread on selective plates (YNB Glycerol containing oligomycin). Cells growing on these plates were considered hybrids or cytoductants, and they were then screened for transfer of desired genetic properties.

Flocculation: Hybrids or cytoductants as generated by methods described above were purified to single colonies on selective plates. Cells were then inoculated in 2-ml YEPD medium in 24-well microtitre plates. The plates were incubated at 30° C. with shaking (150 rpm) for 24 to 48 hours. Flocculation was observed as the accumulation of the majority of the cells in a given well as small granules at the bottom of the well.

Flocculation could also be visualized in flasks containing liquid medium, such as, for example, YEPD, YEPS, buffered YNBG, molasses, etc. Genetically improved hybrids (cytoductants) were grown in YEPD for 16 hours 30° C. Cells from this culture were inoculated separately into 100 ml of clarified molasses in conical flasks, incubated at 30° C. with shaking (150 rpm). Growth and fermentation, as determined by the loss of weight of the flasks, was monitored at regular intervals up to 24 hours. The contents of each flask were quickly poured into graduated measuring cylinders. The time taken for the flocculated cells to sediment to the bottom was recorded with the help of a stop watch and found to be good.

Ethanol production: The new strain was inoculated in YEPD and incubated at 30° C. with shaking for 15 to 24 hours. Samples from each were added to fresh YEPD medium containing 17% (w/v) sugar. The flasks were incubated at 30° C. with shaking. Samples were withdrawn at regular intervals, and incubation was continued for up to 48 hours. The sugar content and alcohol concentration produced in each sample were determined by standard anthrone method and potassium dichromate methods, respectively. This strain produces between about 7% to about 12% alcohol.

EXAMPLE 3

*Saccharomyces crevisiae* MTCC Y0001 (=NCYC 2646) was grown in YM (yeast extract, peptone, malt extract, dextrose, distilled water) medium. Cells were harvested and spread over sporulation medium and incubated at 32° C., and samples were observed under the microscope to monitor the progress of sporulation (which usually takes 4 to 10 days). The asci were then harvested, treated with zymolyase to liberate the spores, and a random spore suspension was made. Strain MTCC Y0002 (=ATCC 90506) was grown in YEPD.

Suspensions of the two strains were mixed in a 1:1 ratio and centrifuged. The pellet was kept at room temperature (25° C.) for two hours, after which it was inoculated in YEPD medium. Cells from the above culture were harvested and spread on selective plates (YNB Glycerol containing oligomycin). Cells growing on these plates were considered hybrids or cytoductants, and were screened for transfer of desired genetic properties.

Flocculation: Hybrids or cytoductants as generated by methods described above were purified to single colonies on selective plates. Cells were then inoculated into 2 ml YEPD medium in 24-well microtitre plates. The plates were incubated at 30° C. with shaking (150 rpm) for 24 to 48 hours. Flocculation was observed as the accumulation of the majority of the cells in a particular well as small granules at the bottom of the wells.

Flocculation could also be visualized in flasks containing liquid medium, such as, YEPD, YEPS, buffered YNBG, molasses, etc. Genetically improved hybrids (cytoductants) were grown in YEPD for 16 hours at 30° C. Cells from these cultures were inoculated separately into 100 ml of clarified molasses in conical flasks and incubated at 30° C. with shaking (150 rpm). Growth and fermentation, as determined by the loss of weight of the flasks, was monitored at regular intervals up to 24 hours. The contents of each flask were quickly poured into graduated measuring cylinders. The time taken for the flocculent cells to sediment to the bottom was recorded with the help of a stop watch and found to be good.

The new strain was inoculated into YEPD medium and incubated at 30° C. with shaking for 15 to 24 hours. Samples from each were added to fresh YEPD medium containing 17 percent sugar. The flasks were incubated at 30° C. with shaking. Samples were withdrawn at intervals and incubation continued up to 48 hours. The sugar content and alcohol concentration produced in each sample was determined by standard anthrone method and potassium dichromate method, respectively. This strain produces between about 7% to about 12% alcohol.

ADVANTAGES OF THE INVENTION

1. The new strain of yeast produced by the process has flocculent characteristics and, as a result, the majority of the cells in a culture sediment to the bottom when agitation is stopped.

2. Since cells are already grown up in the process, less sugar is utilized for further growth; this leads to sugar availability for conversion into alcohol in a continuous or recycling on repeated batch fermentation mode.

3. The strain is more osmotolerant and more ethanol tolerant than conventional strains. As a result, it produces higher levels of alcohol compared to conventional yeast strains without any loss of its ability to convert sugar to alcohol.

4. Because of the above properties, higher initial sugar concentration can be used for fermentation. Consequently, for a given capacity manufacturing plant, the alcohol output may be higher depending on the conditions used.

5. Because of the high alcohol content in the wash, which is achieved by high gravity fermentation, there is a substantial reduction in steam consumption in the recovery process. Net saving of steam in distillation process can be between 0.8 kg to 1.2 kg per liter of alcohol distilled.

6. Consequent to high gravity fermentation, there is a net reduction in effluent volume. This may result in a more compact effluent treatment plant.

The new strain is genetically marked and because of this, the strain is easily identifiable.

We claim:

1. A strain of the yeast *Saccharomyces cerevisiae* having accession number MTCC Y0022B211 (=NCYC 2647) which is useful for the production of ethanol by the fermentation of sugars.

2. A process for the preparation of a strain of the yeast *Saccharomyces cerevisiae* having accession number MTCC Y0022B211 (=NCYC 2647), which comprises a. growing a diploid strain of *S. cerevisiae* designated MTCC Y0001 (=NCYC 2646), sporulating the strain, treating the sporulated cells with a lytic enzyme to liberate the sporulated cells, and collecting the liberated spores;

b. growing a haploid strain of *S. cerevisiae* designated MTCC Y0002 (=ATTC 90506) and collecting the cells;

c. mixing the spores obtained in step (a) with the cells obtained in step (b) and incubating the resultant spore-cell mixture at a temperature in the range of about 15° C. to about 37° C. for a period of about 1 to about 10 days;

d. spreading the incubated spore-cell mixture obtained in step (c) on a non-selective medium and incubating the mixture at a temperature in the range of about 15° C. to about 37° C. for a period of about 1 to about 10 days;

e. collecting the cells produced in step (d) and spreading the collected cells on a selective medium so as to eliminate the spores and cells of steps (a) and (b) and allow only hybrid cells to grow; and f. purifying the hybrid cells.

3. A process as defined in claim 2, wherein the haploid strain MTCC Y0002 used in step (b) is selected from the group consisting of a haploid strain and haploid cells obtained from diploid strains.

4. A process as defined in claim 2, wherein the haploid strain in step (b) is grown in YEPD (Yeast extract, Peptone, Dextrose) medium at a temperature in the range of about 15° C. to about 35° C. for a period of about 1 to about 10 days.

5. A process as defined in claim 2, wherein the incubating in steps (c) and (d) is carried out at a temperature in the range of about 15° C. to about 37° C. for a time period in the range of about 1 to about 10 days.

6. A process as defined in claim 2, wherein the selective medium used in step (e) is SDG (yeast nitrogen base, dextrose, glycerol, agar and distilled water) medium fortified with a broad-range antibiotic selected from the group consisting of geniticin, oligomycin, chloramphenicol, and combinations thereof.

* * * * *